United States Patent [19]

Cordi et al.

[11] Patent Number: 5,464,859

[45] Date of Patent: Nov. 7, 1995

[54] BENZOSPIROALKENE DERIVATIVES

[75] Inventors: Alex Cordi, Suresnes; Jean-Michel Lacoste, Sevres; Michel Laubie, Vaucresson; Tony Verbeuren, Vernouillet; Jean-Jacques Descombes, Neuilly-Plaisance, all of France

[73] Assignee: Adir et Compagnie, Courbevoie, France

[21] Appl. No.: 276,909

[22] Filed: Jul. 19, 1994

[30] Foreign Application Priority Data

Jul. 20, 1993 [FR] France ................... 93 08860

[51] Int. Cl.⁶ ............. A61K 31/415; C07D 491/107; C07D 495/10; C07D 235/02
[52] U.S. Cl. ............. 514/401; 514/402; 548/301.1
[58] Field of Search ............. 548/301.1; 514/401, 514/402

[56] References Cited

FOREIGN PATENT DOCUMENTS 9305045  3/1993  WIPO .

*Primary Examiner*—Patricia L. Morris
*Attorney, Agent, or Firm*—Gordon W. Hueschen

[57] ABSTRACT

Compounds of formula (I):

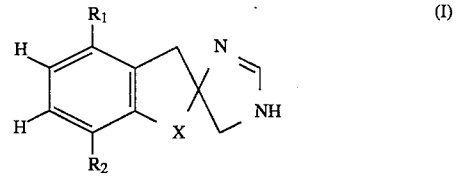

wherein:
—X represents —$CH_2$—, —$(CH_2)_2$—, —CH=CH—, —O—$CH_2$—, —S—$CH_2$—, —SO—$CH_2$— or —$SO_2$—$CH_2$—,
—$R_1$ represents hydrogen or halogen or linear or branched ($C_1$–$C_6$)alkoxy,
—$R_2$ represents linear or branched ($C_1$–$C_6$)alkoxy or linear or branched ($C_1$–$C_6$)alkylthio,
their isomers and their addition salts with a pharmaceutically acceptable acid, and medicinal product containing the same are useful as $\alpha_1$ adrenergic agonist.

4 Claims, No Drawings

BENZOSPIROALKENE DERIVATIVES

The present invention relates to new benzospiroalkenes.

The adrenergic nervous system plays a significant role at a number of levels, for example arterial, venous, cardiac, renal and at the level of the peripheral and central autonomous nervous system. Consequently, products capable of interacting with adrenergic receptors can induce a large number of physiological responses such as vasoconstriction, vasodilation, increase or reduction in the heart rate, and variation in the force of contraction of the cardiac muscle and metabolic activities. Various adrenergic compounds have been used in the past for modifying these or other physiological responses.

In the central nervous system, adrenergic stimulation is particularly useful for compensating for the decline in neurotransmission induced in the locus ceruleus by age, depression or degenerative diseases.

The compounds described in the present invention, in addition to the fact that they are novel, have an $\alpha_1$-adrenergic agonist profile. This property makes them useful, as was shown by P. Timmermans et at. in "Comprehensive Medicinal Chemistry" (Vol. III, p. 134–185, 1990—edited by C. Hansh, Pergamon, Oxford 1990) and J. Nozulak et at. (J. Med. Chem., 35, 480–489, 1992), as sympathomimetics, in the treatment of hypotension, hypersomnia and vigilance and memory disorders, as well as as vasoconstrictors and for curing the symptoms which appear in degenerative diseases such as Alzheimer's disease, Parkinson's disease and Huntingdon's chorea. The therapeutic usefulness of the products of the invention is based on their selectivity for adrenergic receptor subtypes and their selective adjustment of adrenergic functions in various tissues and organs.

More specifically, the present invention relates to the compounds of formula I:

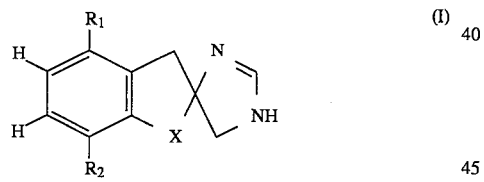

wherein:
- —X represents —CH$_2$—, —(CH$_2$)$_2$—, —CH═CH—, —O—CH$_2$—, —S—CH$_2$—, —SO—CH$_2$— or —SO$_2$—CH$_2$—,
- —R$_1$ represents a hydrogen or halogen atom or a linear or branched (C$_1$–C$_6$)alkoxy group,
- —R$_2$ represents a linear or branched (C$_1$–C$_6$)alkoxy or linear or branched (C$_1$–C$_6$)alkylthio group, to their isomers and to their addition salts with a pharmaceutically acceptable acid.

Mention may be made, among pharmaceutically acceptable acids, without implied limitation, of hydrochloric, hydrobromic, sulfuric, phosphoric, acetic, lactic, malonic, succinic, fumaric, tartaric, maleic, citric and methanesulfonic acids and the like.

Mention may be made, among possible isomers of the compounds of formula (I), of enantiomers, diastereoisomers, epimers and tautomers.

The invention also covers the process for the preparation of the compounds of formula (I), wherein a compound of formula (II):

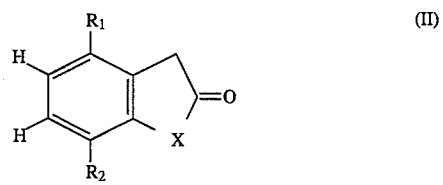

in which X, R$_1$ and R$_2$ have the same meaning as in the formula (I) is used as starting material and is reacted:

either with benzylamine in the presence of para-toluenesulfonic acid to lead to the compound of formula (III):

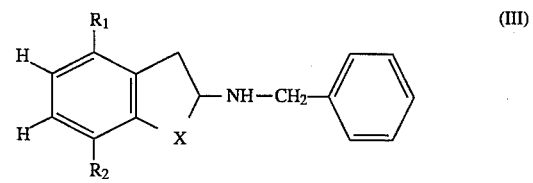

in which X, R$_1$ and R$_2$ have the same meaning as in the formula (I) which is reacted, under an inert atmosphere, with trimethylsilyl cyanide in the presence of zinc iodide, to lead to the compound of formula (IV):

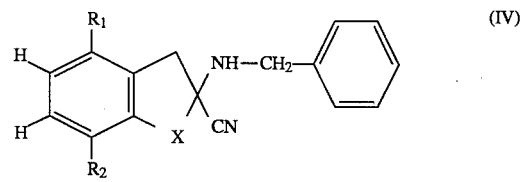

in which X, R$_1$ and R$_2$ have the same meaning as in the formula (I), which is reduced using lithium aluminum hydride and then by catalytic hydrogenation to lead to the compound of formula (V):

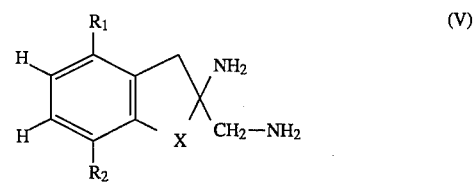

in which X, R$_1$ and R$_2$ have the same meaning as in the formula (I), or with potassium cyanide in the presence of ammonium chloride in an inert medium or with sodium cyanide in an acidic medium, or else with trimethylsilyl cyanide in the presence of zinc iodide and then with a saturated alcoholic ammonia solution, to lead to the compound of the formula (VI):

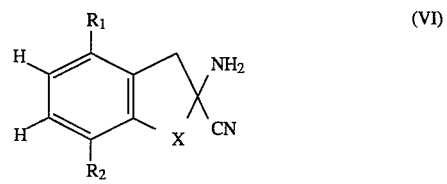

in which X, R$_1$ and R$_2$ have the same meaning as in the formula (I), which is reduced using lithium aluminum hydride to lead to the compound of formula (V) described above, which compound of formula (V) is reacted with formamidine in an alcoholic medium or an alkyl formate, to lead to the compound of formula (I), which is purified, if appropriate, according to a conventional purification technique, the isomers of which are separated, if desired, according to a conventional purification technique, and which are optionally converted to their addition salts with a pharmaceutically acceptable acid.

Another subject of the present invention is the pharmaceutical compositions o containing, as active principle, at least one compound of general formula (I) or one of its addition salts with a pharmacologically acceptable acid, alone or in combination with one or more inert and nontoxic excipients or vehicles.

Mention may more particularly be made, among pharmaceutical compositions according to the invention, of those which are suitable for oral, parenteral or nasal administration, simple or sugar-coated tablets, sublingual tablets, gelatin capsules, lozenges, suppositories, creams, ointments, dermal gels and the like.

The dose varies according to the age and weight of the patient, the nature and the severity of the complaint, and the administration route.

The latter can be oral, nasal, rectal or parenteral. The unit dose will generally range between 0.1 and 1000 mg for a treatment taken 1 to 3 times per 24 hours.

The following examples illustrate the invention. The starting materials used are known products or products prepared according to known procedures.

The product described in Preparation A leads to a starting material which is useful in the preparation of a compound of the invention.

Preparation A

5-Methylthio-8-methoxy-3,4-dihydronaphthalen-2(1H)-one

Stage A: Spiro[(1,3-dioxolane)-2,2'-(8'-methoxy-1',2',3',4'-tetrahydronaphthalene)]

A solution containing 69 mmol of 8-methoxy-3,4-dihydronaphthalen-2(1H)-one, 75 mmol of ethylene glycol and 100 mg of p-toluenesulfonic acid in 500 ml of toluene is brought to reflux with azeotropic distillation of the water/toluene mixture for 3 hours. After cooling and evaporation under vacuum, the residue is taken up in 100 ml of ethyl ether. After washing with water and evaporation, the expected product is obtained in the form of an oil by distillation of the residue under vacuum.

Boiling point: 122°–125° C. (p=1.33 Pa)

Stage B: Spiro[(1,3-dioxolane)-2,2'-(5'-iodo-8'-methoxy-1',2',3',4'-tetrahydronapthalene)]

A solution of 108 mmol of iodine in 1 liter of acetic acid and a solution of 56 mmol of mercuric diacetate in 1 liter of acetic acid are added dropwise and simultaneously, at a temperature not exceeding 55° C., to a solution, heated to 50° C., containing 35 mmol of the compound obtaining in the preceeding stage in 200 ml of acetic acid. The whole mixture is stirred for 30 minutes at this temperature and then for 2 hours at 20° C. The acetic acid is evaporated under vacuum and the residue taken up in a 10% potassium iodide solution. After filtration, the residue is taken up in an ammonia solution and extracted with dichloromethane. The organic phase is dried, evaporated and leads to the expected product in the solid form.

Melting point 88°–90° C.

Stage C: Spiro[(1,3-dioxolane)-2,2'-(5'-methylthio-8'-methoxy-1',2',3',4'-tetrahydronaphthalene)]

18 mmol of the compound obtained in the preceeding stage, in 90 ml of dimethyl sulfoxide (DMSO), and then 286 mmol of cuprous oxide are added to a suspension containing 184 mmol of freshly prepared lithium methanethiolate in 180 ml of DMSO. The mixture is stirred for 5 hours at 80° C. under a nitrogen atmosphere. After cooling, the precipitate is filtered, the filtrate is concentrated and the residue thus obtained is taken up in dichloromethane. The organic phase is washed with water, dried and evaporated. The expected product is then obtained after purification of the residue by chromatography on a silica column, dichloromethane being used as eluent.

Melting point: 42°–44° C.

Stage D: 5-Methylthio-8-methoxy-3,4-dihydronaphthalen-2(1H)-one

A solution containing 20 mmol of the compound obtained in the preceeding stage in 50 ml of a 30% aqueous acetic acid solution is heated for 3 hours at 90° C. After cooling, the mixture is poured onto ice-cold water. The expected product is obtained by filtering the precipitate and washing with water.

Melting point: 88°–90° C.

EXAMPLE 1

Spiro[(1,3-diazacyclopent-1-ene)-5,2'-(5',8'-dimethoxy-1',2',3',4'-tetrahydronaphthalene)]fumarate Stage A: 2-Benzylamino-5,8-dimethoxy-3,4-dihydronaphthalene A mixture containing 82 mmol of 5,8-dimethoxy-3,4-dihydronaphthalen-2(1H)-one, 82 mmol of benzylamine and 0.20 g of p-toluenesulfonic acid is brought to reflux with azeotropic distillation of the water/toluene mixture. After heating for 2 hours, the mixture is cooled, filtered and the solvent evaporated under vacuum and leads to the expected product in the form of an oil.

Stage B: 2-Benzylamino-2-cyano-5,8-dimethoxy-1,2,3,4-tetrahydronaphthalene 80 mmol of trimethylsilyl cyanide and 1 g of zinc iodide are added successively to a solution, maintained under nitrogen, containing 80 mmol of the compound obtained in the preceeding stage in 400 ml of dichloromethane. The mixture is stirred at 20° C. overnight and then washed with water. After drying the organic phase and evaporation, the expected product is obtained in the form of an oil.

Stage C: 2-Benzylamino-2-aminomethyl-5,8-dimethoxy-1,2,3,4-tetrahydronaphthalene 70 mmol of the compound obtained in the preceeding stage in 100 ml of anhydrous tetrahydrofuran (THF) are added dropwise, at a temperature not exceeding 20° C., to a suspension containing 140 mmol of lithium aluminum hydride in 350 ml of anhydrous THF. After stirring for 2 hours, the mixture is cooled to 0° C. and then hydrolyzed by successive addition of 6 ml of water, 6 ml of 2N sodium hydroxide solution and 12 ml of water. The resulting suspension is filtered and the filtrate concentrated. The oily residue thus obtained is dissolved in 200 ml of ethyl acetate. This solution is washed with water and extracted with a 1N hydrochloric acid solution. The aqueous phase is basified with 35% sodium hydroxide solution and extracted with ethyl acetate. After drying and evaporation, the expected product is obtained in the form of an oil.

Stage D: 2-Amino-2-aminomethyl-5,8-dimethoxy-1,2,3,4-tetrahydronaphthalene

A suspension containing 30 mmol of the compound obtained in the preceeding stage, 125 mmol of ammonium formate and 6 g of 10% palladium-on-charcoal in 250 ml of methanol is heated at reflux with stirring for 90 minutes. After cooling, filtration of the catalyst and evaporation of the solvent, the expected product is obtained in the form of an oil.

Stage E: Spiro[(1,3-diazacyclopent-1-ene)-5,2'-(5',8'-dimethoxy-1',2',3',4 '-tetrahyronaphthalene)]fumarate A mixture containing 26 mmol of the compound obtained in the preceeding stage and 27 mmol of formamidine acetate in 150 ml of ethanol is stirred at 20° C. under nitrogen for 10, hours. After evaporation of the solvent, the residue is taken up in 100 ml of 1N hydrochloric acid. This organic phase is washed with ethyl acetate and basified with 35% sodium hydroxide solution. After extraction with ethyl acetate, the organic phases are washed with a saturated sodium chloride solution, concentrated and lead to a solid residue. This residue is dissolved in 80 ml of ethanol treated with one equivalent of fumaric acid dissolved in 50 ml of ethanol. After evaporation of the solvent, the expected product crystallizes from ethanol.

Melting point: 185°–188° C.

| Elemental microanalysis: | C % | H % | N % |
|---|---|---|---|
| calculated | 59.66 | 6.12 | 7.73 |
| found | 59.41 | 6.07 | 7.74 |

Examples 2, 3 and 4 were obtained according to the process described in Example 1 by using the corresponding starting materials.

EXAMPLE 2

Spiro[(1,3-diazacyclopent-1-ene )-5,2'-(5'-ethoxy-8'-methoxy-1',2',3',4' -tetrahydronaphthalene)] fumarate Melting point: 174°–178° C.

| Elemental microanalysis: | C % | H % | N % |
|---|---|---|---|
| calculated | 58.06 | 6.03 | 6.45 |
| found | 58.07 | 6.10 | 6.50 |

EXAMPLE 3

Spiro[(1,3-diazacyclopent-1-ene)-5,2'-(5',8'-diethoxy-1',2',3',4 '-tetrahydronaphthalene) fumarate Melting point: 196°–198° C.

| Elemental microanalysis: | C % | H % | N % |
|---|---|---|---|
| calculated | 61.53 | 6.71 | 7.17 |
| found | 61.40 | 6.97 | 7.06 |

EXAMPLE 4

Spiro[(1,3-diazacyclopent-1-ene)-5,2'-(4',7'-dimethoxyindane)]½ fumarate

Melting point: 224°–228° C.

| Elemental microanalysis: | C % | H % | N % |
|---|---|---|---|
| calculated | 62.06 | 6.25 | 9.65 |
| found | 61.50 | 6.24 | 9.43 |

EXAMPLE 5

Spiro[(1,3-diazacyclopent-1-ene)-5,2'-(5'-methoxy-1',2',3',4 '-tetrahydronaphthalene)]

Stage A: 2-Amino-2-cyano-5-methoxy-1,2,3,4-tetrahydronaphthalene 112 mmol of potassium cyanide and 116 mmol of ammonium chloride ate added successively to a solution, maintained under nitrogen and with stirring, containing 110 mmol of 5-methoxy-3,4-dihydronaphthalen-2(1H)-one in 90 ml of ethanol and 50 ml of water. The whole mixture is stirred for 20 hours at 20° C. and then concentrated under vacuum. The residue is taken up in 200 ml of ethyl acetate. This phase is then washed with water and extracted with 1N hydrochloric acid. The acid phase is basified with 35% sodium hydroxide solution and extracted with methyl acetate. The combined organic phases are dried and evaporated under vacuum and lead to the expected product in the solid form.

Melting point: 97° C.

Stage B: 2-Amino-2-aminomethyl-5-methoxy-1,2,3,4-tetrahydronaphthalene

A solution containing 70 mmol of the compound described in the preceeding stage in 80 ml of THF is added dropwise, at a temperature not exceeding 20° C., to a suspension containing 162 mmol of lithium aluminum hydride in 200 ml of anhydrous THF. After stirring for 1 hour, the mixture, cooled to 0° C., is hydrolyzed by successive addition of 5.5 ml of water, 5.5 ml of 2N sodium hydroxide solution and 96 ml of water. The resulting suspension is filtered and the filtrate evaporated. The oily residue is then dissolved in 250 ml of ethyl acetate. This phase is washed with water and extracted with 1N hydrochloric acid. The aqueous phases are then basified with 35% sodium hydroxide solution and extracted with ethyl acetate. After drying and evaporation of the organic phases, the expected product is obtained in the form of an oil.

Stage C: Spiro[(1,3-diazacyclopent-1-ene)-5,2'-(5'-methoxy-1',2',3',4 '-tetrahydronaphthalene)]

The expected product is obtained, according to the process described in Stage E of Example 1, from the compound described in the preceeding stage.

Melting point: 188°–190° C.

| Elemental microanalysis: | C % | H % | N % |
|---|---|---|---|
| calculated | 61.44 | 6.07 | 8.43 |
| found | 61.23 | 6.02 | 8.34 |

EXAMPLE 6

Spiro[(1,3-diazacyclopent-1-ene)-5,2'-(5'-methylthio-8'-methoxy-1',2',3',4'-tetrahydronaphthalene)]fumarate Stage A: 2-Amino-2-cyano-5-methylthio-8-methoxy-1,2,3,4-tetrahydronaphthalene 1 ml of concentrated hydrochloric acid is added dropwise with stirring to a mixture containing 9 mmol of the compound described in Preparation A and 29 mmol of sodium cyanide in 50 ml of water and 40 ml of ethyl ether. After stirring for 1 hour at 20° C., the organic phase is separated by settling, washed with water, dried and evaporated. The oil obtained is then treated with a methanolic ammonia solution (3.5M), with stirring, in a closed environment, for 6 hours at 20° C. After evaporation of the solvent, the oil is taken up in ethyl ether and extracted with 1N hydrochloric acid. The aqueous phases are basified with 35% sodium hydroxide solution and then extracted with ethyl ether. The expected product is then obtained in the solid form after drying and evaporation of the organic phase.

Melting point: 128°–130° C.

Stage B: 2-Amino-2-aminomethyl-5-methylthio-8-methoxy-1,2,3,4-tetrahydronaphthalene The expected product is obtained according to the process described in Stage B of Example 5 by using the compound described in the preceeding stage.

Stage C: Spiro[(1,3-diazacyclopent-1-ene)-5,2'-(5'-methylthio-8-methoxy-1',2',3',4'-tetrahydronaphthalene)]fumarate The expected product is obtained according to the process described in Stage C of Example 5 by using the compound described in the preceeding stage.

Melting point: 188°–190° C.

| Elemental microanalysis: | C % | H % | N % | S % |
|---|---|---|---|---|
| calculated | 57.13 | 5.86 | 7.40 | 8.47 |
| found | 57.05 | 6.01 | 7.50 | 8.53 |

EXAMPLE 7

Spiro[(1,3-diazacyclopent-1-ene)-5,2'-(5',8'-dimethoxy-1',2',3',4'-tetrahydro-naphthalene)] fumarate, isomer α

The expected product is obtained by resolution of the compound described in Example 1 using [+]-dibenzoyl-D-tartaric acid and by successive recrystallizations from ethanol. The enantiomeric purity is monitored by Diacelog chiral column chromatography, using an isopropanol/n-heptane/dithylamine (20/80/0.1) mixture as eluent. The salt is then shared between 1N sodium hydroxide solution and dichloromethane. The aqueous phase is extracted with dichloromethane. After drying and evaporation of the organic phases, the residue is taken up in an ethanolic solution containing one equivalent of fumaric acid and the whole mixture is brought to reflux. The expected product is obtained after cooling and filtration in the form of a white solid.

Melting point: 187°–188° C.

| Elemental microanalysis: | C % | H % | N % |
|---|---|---|---|
| calculated | 59.66 | 6.12 | 7.73 |
| found | 59.59 | 6.08 | 7.65 |

EXAMPLE 8

Spiro[(1,3-diazacyclopent-1-ene)-5,2'-(5',8'-dimethoxy-1',2',3',4'-tetrahydronaphthalene)]fumarate, isomer β

The expected product is obtained according to the process described in Example 7 by resolution of the compound described in Example 1 using [-]-dibenzoyl-L-tartaric acid.

Melting point: 187°–188° C.

| Elemental microanalysis: | C % | H % | N % |
|---|---|---|---|
| calculated | 59.66 | 6.12 | 7.73 |
| found | 59.36 | 6.09 | 7.74 |

PHARMACOLOGICAL STUDY OF THE COMPOUNDS OF THE INVENTION

EXAMPLE 9

In vitro study on the femoral arteries and saphenous veins of dogs

The technique used is based on that described by Fowler et at. (J. Pharmacol. Exp. Ther., 229, 712–718, 1984). Male or female mongrel dogs weighing approximately 15–25 kg were used as organ sources. The animals are anesthetized with pentrobarbital (30 mg/kg, intravenously). Incisions are made in the legs and the vessels are withdrawn. They are placed in Krebs-Ringer liquid (NaCl 118 mM, NaHCO$_3$ 25 mM, Glucose 10 mM, KCl 4.7 mM, CaCl$_2$ 1.25 mM, MgSO$_4$ 1.19 mM, KH$_2$PO$_4$ 1.14 mM) at room temperature and while bubbling with carbogen (95% O$_2$, 5% CO$_2$). These vessels are then carefully freed from their fat, then cut into rings with a width of 2 mm and mounted under a base tension of 4 g (femoral arteries) or 1 g (saphenous veins) in vessels thermostatically controlled at 37° C. containing Krebs-Ringer liquid through which carbogen is constantly bubbling. A lower hook constitutes the set point whereas the upper hook is connected to an isometric force sensor. The tension variations are digitized, stored on disk and processed by a computer system. After mounting, the organs, are left at rest for 90 minutes, rinsings being carried out every 30 min. After readjusting the base tension, a contraction is caused by a single dose of KCl (100 mM). After stabilisation, washing and returning to the base line, a contraction is provoked by a single dose of phenylephrine (submaximal concentration) in order to regularize the following contractions. After washing and returning to the base line, a concentration/effect curve is produced by addition of cumulative doses of agonist (the spacing between the doses is a half-log). This experiment makes it possible to calculate the 50% effective concentration (EC$_{50}$) in the following way: the tension values are first converted to percentages with respect to the maximum effect caused by 100 mM of KCl. This EC$_{50}$ is determined by non-linear regression by the Simplex method (M. S. Caceci, Byte, 340–362, 1984), calculated according to the model of the law of mass action of L. Michaelis and M. L. Menten (Biochem. Zeitschrifft, 49, 333–369, 1913). $E=(E_{max}*C^n)(EC^n+C^n)$ where E=effect, Emax=maximum effect, C=concentration, $EC=EC_{50}$ and n=Hill number.

The products of the invention contract the arteries and veins of dogs. The maximum of these contractions approaches that obtained with KCl. The results obtained are presented in the table below:

| Example | ARTERY | | VEIN | |
| --- | --- | --- | --- | --- |
| | $EC_{50}$ (μM) | Max (% KCl) | $EC_{50}$ (μM) | Max (% KCl) |
| 1 | 0,16 | 72 | 0,2 | 100 |
| 5 | 1,5 | 93 | 6,4 | 100 |
| 6 | 0,08 | 85 | 0,8 | 98 |
| 7 | 0,03 | 95 | 0,12 | 109 |

EXAMPLE 10

In vivo study on AMYELOUS RATS

Male Sprague-Dawley rats (300–400 g) are anesthatized with ether. A cannula is inserted in the trachea, the spinal cord is destroyed using a steel rod and the animal is immediately placed under artificial respiration. The vagus nerves are sectioned. The carotid arteries are ligatured and a catheter is placed in one and is used to record the arterial pressure. Three other catheters are placed in the jugular veins and the vein of the penis and are used for injections. The temperature of the animals is maintained at 36° C. The animal is pretreated with an injection of tertatolol (100 g/kg). The animal is also pretreated 10 minutes afterwards with prazosin (100 g/kg) or yohimbine (1 mg/kg) when it is wished to determine the $_1$ or $_2$-adrenergic properties of the product. Ten minutes later, increasing cumulative doses of product are injected every 20 seconds. The medal pressure variations are detected using a P23XL Statham pressure cell and are recorded. The pressure values are expressed in mmHg. This experiment makes it possible to calculate the concentration which increases the pressure by 20 mmHg ($C_{20}$) by non-linear regression according to the model of the Michaelis and Menten mass action law as described above. The maximum effect obtained is then converted to a percentage with respect to the maximum effect caused by phenylephrine. The $_1$ or $_2$-adrenergic components of the product are estimated using the ratio of the $C_{20}$ values obtained in the presence of prazosin or of yohimbine to the values obtained in the absence of these antagonists. In amyelous rats, the products of the invention induce hypertensions which are inhibited more by prazosin than by yohimbine. The results are collected in the table below:

| Example | $C_{20}$ (μg/kg) Control | Ratio $C_{20}$ treated/$C_{20}$ control | |
| --- | --- | --- | --- |
| | | Prazosin | Yobimbine |
| 1 | 0,009 | 97 | 11 |
| 2 | 0,06 | 22 | 5 |
| 3 | 0,6 | 24 | 8 |

EXAMPLE 11

Pharmaceutical composition

Formula for the preparation of 1000 tablets containing a dose of 10 mg

| | |
| --- | --- |
| Compound of Example | 10 g |
| Hydroxypropyl cellulose | 2 g |
| Wheat starch | 10 g |
| Lactose | 100 g |
| Magnesium stearate | 3 g |
| Talc | 3 g |

We claim:
1. A compound of formula (I):

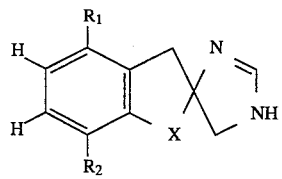

wherein:
—X represents —$CH_2$—, —$(CH_2)_2$—, —CH═CH—, —O—$CH_2$—, —S—$CH_2$—, —SO—$CH_2$—, or —$SO_2$—$CH_2$—, —$R_1$ representshydrogen or halogen or linear or branched ($C_1$-$C_6$) alkoxy, —$R_2$ represents linear or branched ($C_1$-$C_6$)alkoxy or linear or branched ($C_1$-$C_6$) alkylthio, its isomers or its addition salts with a pharmaceutically-acceptable acid.

2. A compound of claim 1 selected from those in which X represents —$(CH_2)_2$—, its isomers or its addition salts with a pharmaceutically-acceptable acid.

3. A compound of claim 1 which is selected from spiro [(1,3-diazacylopent-1-ene)-5,2'-(5',8'-dimethoxy-1',2',3',4'-tetrahydronaphthalene)], its isomers, and its addition salts with a pharmaceutically-acceptable acid.

4. A pharmaceutical composition useful as an $\alpha_1$ adrenergic agonist comprising as active principle an effective amount of a compound of claim 1, together with a pharmaceutically-acceptable excipient or vehicle.

* * * * *

UNITED STATES PATENT AND TRADEMARK OFFICE
CERTIFICATE OF CORRECTION

PATENT NO. : 5,464,859
DATED : Nov. 7, 1995                                Page 1 of 4
INVENTOR(S) : Alex Cordi, Jean-Michel Lacoste, Michel Laubie,
Tony Verbeuren, Jean-Jacques Descombes It is certified that error appears in the above-indentified patent and that said Letters Patent is hereby corrected as shown below:

Column 1, line 25: "et at." should read -- et al. --
   Pg. 1, line 15

Column 2, line 18 (approx.): Line missing in formula (see below).

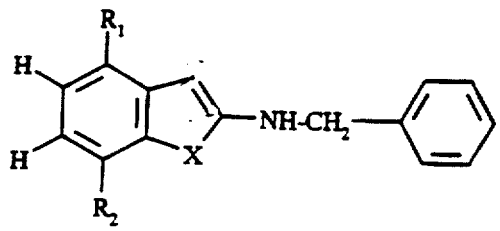

Column 3, line 12: Delete "o".

Column 4, line 28: Delete "1',2',3',4" at end of line. Pg.

Column 4, line 29: Add -- 1',2',3',4 -- at beginning of line.

Column 5, line 39: Add -- )- -- at end of line.

Column 5, line 40: Delete ")-" from beginning of line and add "-" (dash) at end of line.

UNITED STATES PATENT AND TRADEMARK OFFICE
CERTIFICATE OF CORRECTION

PATENT NO. : 5,464,859
DATED : Nov. 7, 1995
INVENTOR(S) : Alex Cordi, Jean-Michel Lacoste, Michel Laubie, Tony Verheuzen, Jean-Jacques Descombes It is certified that error appears in the above-indentified patent and that said Letters Patent is hereby corrected as shown below:

Column 5, line 41: Delete "-" (dash) from beginning of line.

Column 5, line 57: Delete "1',2',3',4" from end of line.

Column 5, line 58: Add -- 1',2',3',4 to beginning of line.

Column 6, line 17 (approx.): Add -- ' -- to end of line.

Column 6, line 18 (approx.): Delete "'-" from beginning of line.

Column 6, line 24: "ate" should read -- are --.

Column 7, line 4: Delete "[" from end of line.

Column 7, line 5: Add "[" to beginning of the line and delete "1',2',3',4'" from end of the line.

Column 7, line 6: Add -- 1',2',3',4' -- to beginning of the line.

UNITED STATES PATENT AND TRADEMARK OFFICE
CERTIFICATE OF CORRECTION

PATENT NO. : 5,464,859
DATED : Nov. 7, 1995
INVENTOR(S) : Alex Cordi, Jean-Michel Lacoste, Michel Laubie, Tony Verbeuren, Jean-Jacques Descombes It is certified that error appears in the above-indentified patent and that said Letters Patent is hereby corrected as shown below:

Column 7, line 8: Add -- - -- (a dash) at end of the line.

Column 7, line 51: Delete "1',2',3',4" from end of the line.

Column 7, line 52: Add -- 1',2',3',4 -- at the beginning of the line.

Column 8, line 11 (approx.): Add -- ' -- at the end of the line.

Column 8, line 12 (approx.): Delete "'-" from the beginning of the line.

Column 8, line 35: "et. at." should read -- et. al. --.

UNITED STATES PATENT AND TRADEMARK OFFICE
CERTIFICATE OF CORRECTION

PATENT NO. : 5,464,859
DATED : Nov. 7, 1995
INVENTOR(S) : Alex Cordi, Jean-Michel Lacoste, Michel Laubie, Tony Verbeuren, Jean-Jacques Descombes It is certified that error appears in the above-indentified patent and that said Letters Patent is hereby corrected as shown below:

```
Column 10, line 51:   Add a -- , -- (a comma) after
                      "isomers".

Column 10, line 54:   Add -- '- -- at end of line.
                      P.A. dtd 7/19/94,
Column 10, line 55:   Delete "'-" from beginning of
                      the line.
```

Signed and Sealed this

Twelfth Day of March, 1996

Attest:

BRUCE LEHMAN

*Attesting Officer*   Commissioner of Patents and Trademarks